United States Patent [19]

Caillot

[11] 4,380,233

[45] Apr. 19, 1983

[54] CONTROL DEVICE FOR AN ARTIFICIAL RESPIRATOR

[75] Inventor: Luc Caillot, Paris, France

[73] Assignee: Synthelabo, Paris, France

[21] Appl. No.: 221,469

[22] Filed: Dec. 30, 1980

[30] Foreign Application Priority Data

Jan. 4, 1980 [FR] France ................................. 80 00096

[51] Int. Cl.³ .......................................... A61H 31/00
[52] U.S. Cl. ........................ 128/204.21; 128/203.14; 128/205.11
[58] Field of Search ...................... 128/204.21–204.23, 128/203.14, 205.11–205.12, 204.18, 204.29

[56] References Cited

U.S. PATENT DOCUMENTS 3,101,708  8/1963  Perry et al. ..................... 128/204.21
3,768,468 10/1973  Cox ................................ 128/204.21

FOREIGN PATENT DOCUMENTS 1288019  9/1972  United Kingdom ........... 128/204.21

OTHER PUBLICATIONS

*Surgery*, vol. 42, No. 4, Oct. 1957, pp. 722–725, "A Respirator for Laboratory Animals Utilizing Compressed Air and Suction".

*Primary Examiner*—Kyle L. Howell
*Assistant Examiner*—Angela D. Sykes
*Attorney, Agent, or Firm*—Sughrue, Mion, Zinn, Macpeak and Seas

[57] ABSTRACT

A control device for an artificial respirator includes a timebase circuit (B) on which the frequency $F=1/T$ and the ratio I/E of the inhalation to exhalation times are selected, a mixer (M) on which the total gas supply volume and the proportion of oxygen are selected, and two control signal generators ($G_O$, $G_A$) for operating two solenoid-controlled valves ($EV_A$, $EV_O$) for the air and oxygen.

It is possible to select each one of the four variable parameters independently of all the others.

4 Claims, 5 Drawing Figures (GENERATOR G₀ OR Gₐ)

(SOLENOID VALVE)

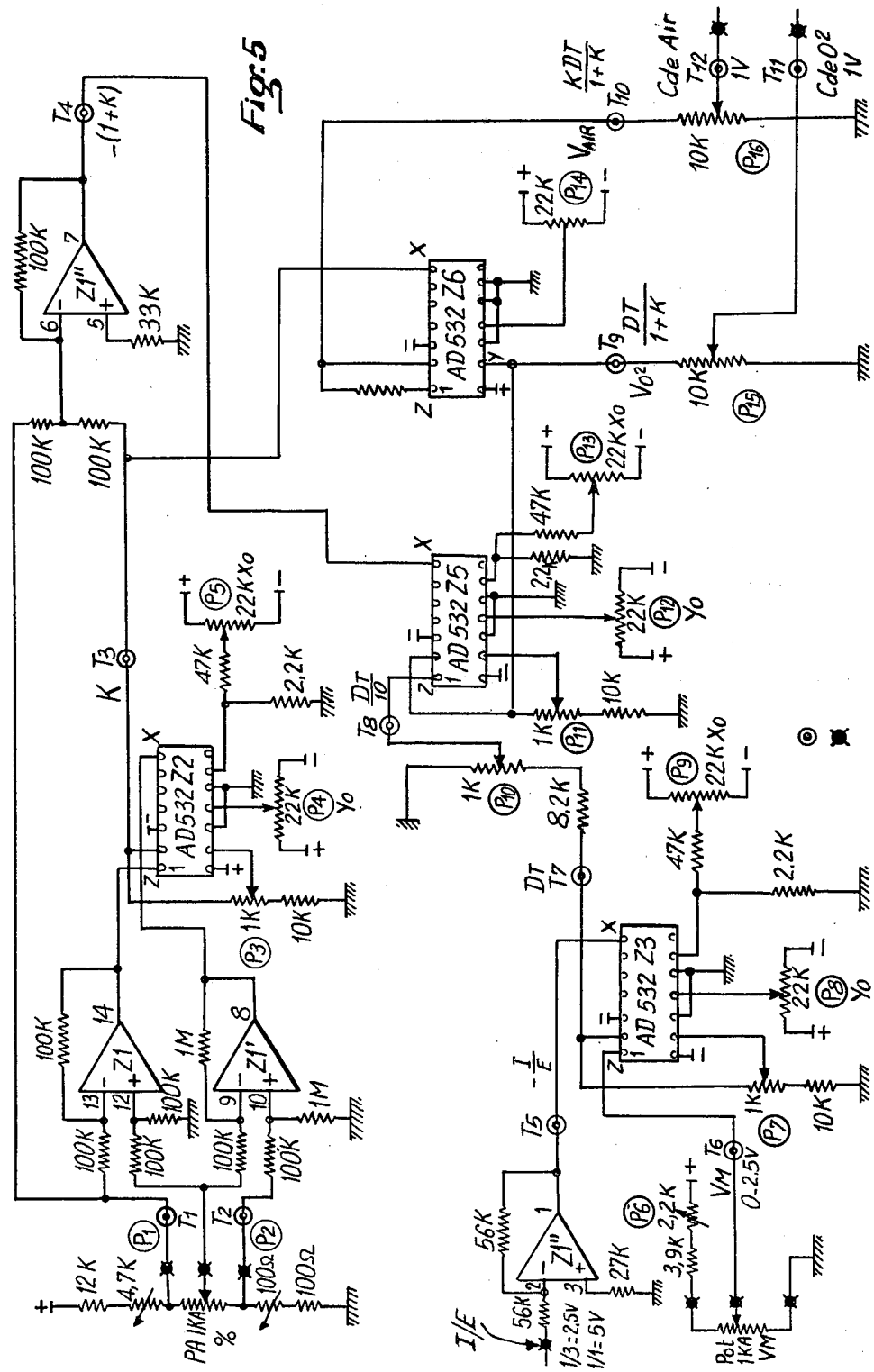

CONTROL DEVICE FOR AN ARTIFICIAL RESPIRATOR

The present invention concerns an artificial respirator and in particular relates to an electronic control device for such a respirator.

Such a device, as is known, is used for the respiration of a patient, particularly when he is under anaesthesia during the course of an operation or undergoing resuscitation or in an intensive care unit for example. The purpose of the apparatus is to supply the patient with air which is often enriched in oxygen, and is consequently a mixture of air and oxygen, at a rhythm corresponding to that of his breathing rate and at a slight over-pressure (several tens of millibars, so as to supplement or reinforce the deficient function). It is important to be able to precisely select the rate of flow of the gas mixture delivered to the patient, the oxygen content of this mixture, the period T of respiration being imposed on him, and, within this period, the inspiration portion and the expiration portion (in other words the cyclic ratio I/E).

Up until now, it was common to use a device including a mechanical mixer, followed by a needle valve for regulating the flow, the mixture issuing from this then passing through a solenoid-controlled valve regulated by a timebase circuit. The main drawback of such a system is that the rate of flow is changed if one makes an alteration in the period, or in the $O_2$ content of the mixture, and it is consequently a long and difficult process to obtain precise adjustments, which in particular are very difficult to modify during the course of an operation.

The present invention provides a control device the parameters of which can be adjusted in a completely independent manner.

According to the present invention, the control device for an artificial respirator comprises: a solenoid-controlled valve for the air and a solenoid-controlled valve for the oxygen, of the variable flow type as a function of the plunger travel, discharging into a manifold; a timebase circuit with a unit for fixing the frequency or the respiratory period and a unit for fixing the ratio I/E of the inspiration time to the expiration time during the period; a mixer, including units for fixing the overall respiratory flow and the proportion of oxygen in the gas supplied by the respirator; and two signal generators each one linked to a solenoid-controlled valve for controlling their opening; the timebase circuit being connected to the generators in order that they may control the opening of the valves during the inspiration period, the generators being further connected to the mixer for receiving signals corresponding to the extent of opening of the valve during the inspiration period, the mixer being connected to the timebase for receiving a signal corresponding to the ratio I/E so as to elaborate with the indications of flow and of proportion, signals for the opening of the valves such that during the inspiration phase, each valve allows a quantity of gas to pass which corresponds to the mean flow rate during the period.

The description which follows, with reference to the attached drawings which are provided by way of non-limiting example, will make it clear how the invention can be put into practice.

FIG. 5 shows an example of a complete arrangement of the electronic circuit with indication of the components and their values.

Figure 1:
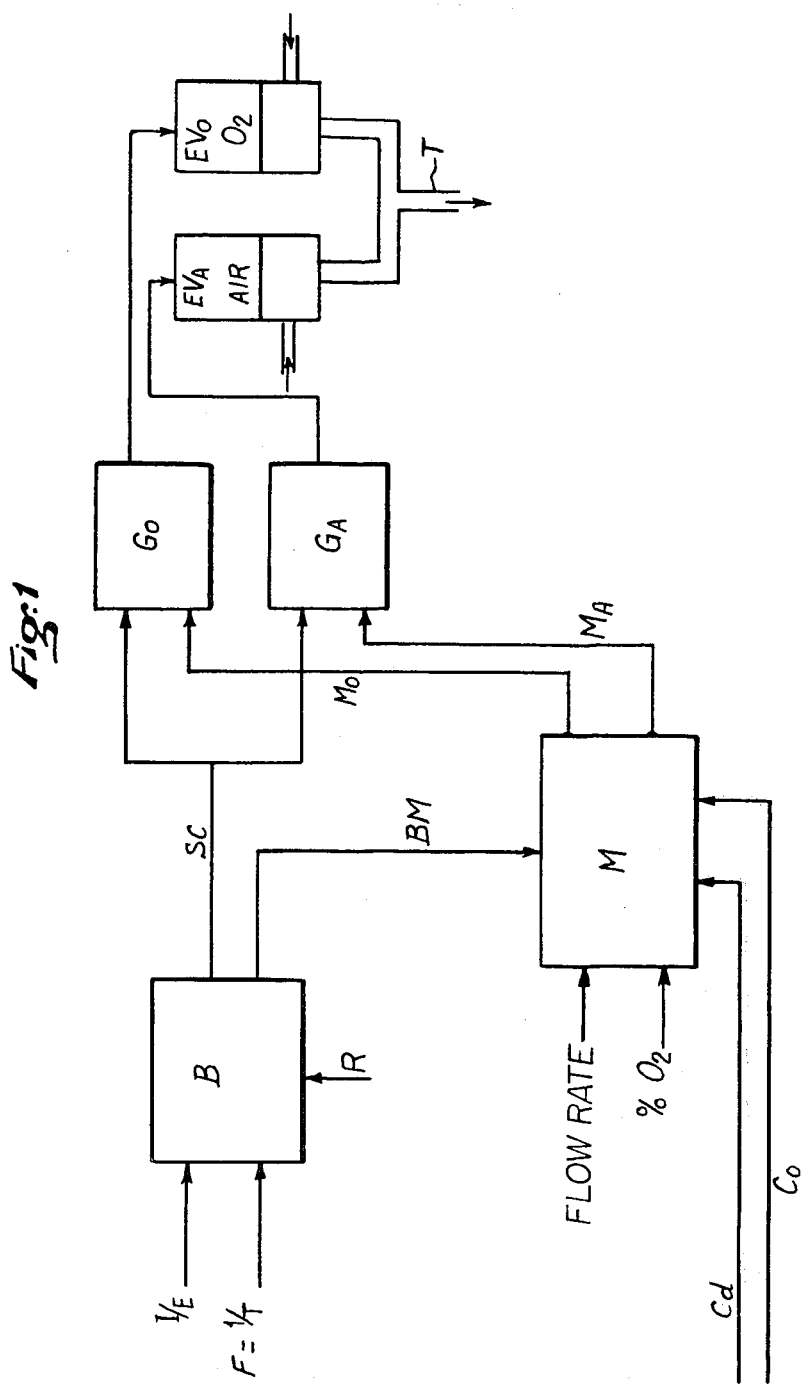
FIG. 1 is a block diagram of the device according to the invention.

The control device for the artificial respirator includes a solenoid-controlled valve for the air $EV_A$ and a solenoid-controlled valve for the oxygen $EV_O$. These solenoid-controlled valves (see FIG. 4 and the description below) are of the variable opening type as a function of the amp-turns supplied to control them; they are supplied with air and with oxygen at pressures which are very precisely regulated. The throughput of air and oxygen is consequently an accurate function of the opening time and the degree of travel of the plunger of each valve. The solenoid-controlled valves discharge into a tube T, which is directly connected to the gas supply circuit to the patient, and constituting part of the respirator, which, concerning its construction, is of any conventional type.

Control signals for the opening of each valve are provided by two signal generators $G_A$ and $G_O$ which are identical and each control one of the valves. The generators $G_A$ and $G_O$ are in their turn controlled by a timebase circuit B, including means allowing the operator to fix both the frequency $F = 1/T$ of respiration, and the cyclic ratio I/E ($E + I = T$) of the inspiration time to the expiration time and, by a mixer M including means for adjusting the total throughput of the air-oxygen mixture to be delivered to the patient, and the proportion of oxygen in this mixture. That is, the timebase circuit output signal is in the form of a periodic pulse signal where the width of each pulse corresponds to the inspiration or inhalation time I and whose frequency F corresponds to the respiration or breathing rate. The dead or zero output time between pulses corresponds to the expiration or exhalation time E. The timebase circuit may furthermore be automatically readjusted by a reaction signal R, originating, for example, from measurements carried out on the patient.

The timebase circuit is connected, by a line SC, to two generators, in order to inject the same chronological signal into them. Using these signals, the generators provide signals for control of the opening of the valves during the time I within each time period T.

The degree of opening of the valves are elaborated by the generators using the signals received from the mixer on the lines $M_O$ and $M_A$. These control signals take into account the flow rate of the mixture and the proportion of oxygen, these being two parameters which are selected by the operator and also a signal related to I/E, which is sent by the timebase circuit to the mixer M on the line BM. It is thus possible to obtain a flow rate, with a percentage of oxygen, which is fixed, whatever the values might be selected by the operator for F and for I/E.

The mixer may furthermore receive external signals for correcting the flow rate and the percentage of oxygen, from lines Cd and Co, for example where automatic monitoring of certain parameters of the patient is being carried out.

Let us now consider the parameters to be determined. If the total throughput, air plus oxygen, is called $D_T$, and $D_O$ and $D_A$ are the respective throughputs of oxygen and air respectively, this leads to:

$$D_T = D_O + D_A \qquad (1)$$

and if the percentage of oxygen in the mixture is called $F_O$, this leads to:

$$F_O = (D_O + 0.21\, D_A)/(D_O + D_A) \qquad (2)$$

The mixer is constructed in such a way that it is possible to regulate $D_T$ and $F_O$ independently of each other. The generation of the electrical signals is carried out according to the present invention using the equations (1) and (2) above. Generation of the control signals can equally well be provided using an analog process or a completely digital process. This latter process may be preferred in the case where automatic control of the parameters is being carried out using an external regulating source. Equation (2) can be re-written as follows:

$$D_A = D_O \frac{(1 - F_O)}{F_O - 0.21} = D_O \cdot K$$

which on re-arrangement gives the following values for $D_O$ and $D_A$ as a function of $D_T$:

$$D_O = \frac{D_T}{1+K} \qquad D_A = D_T \frac{K}{1+K}$$

Figure 2:
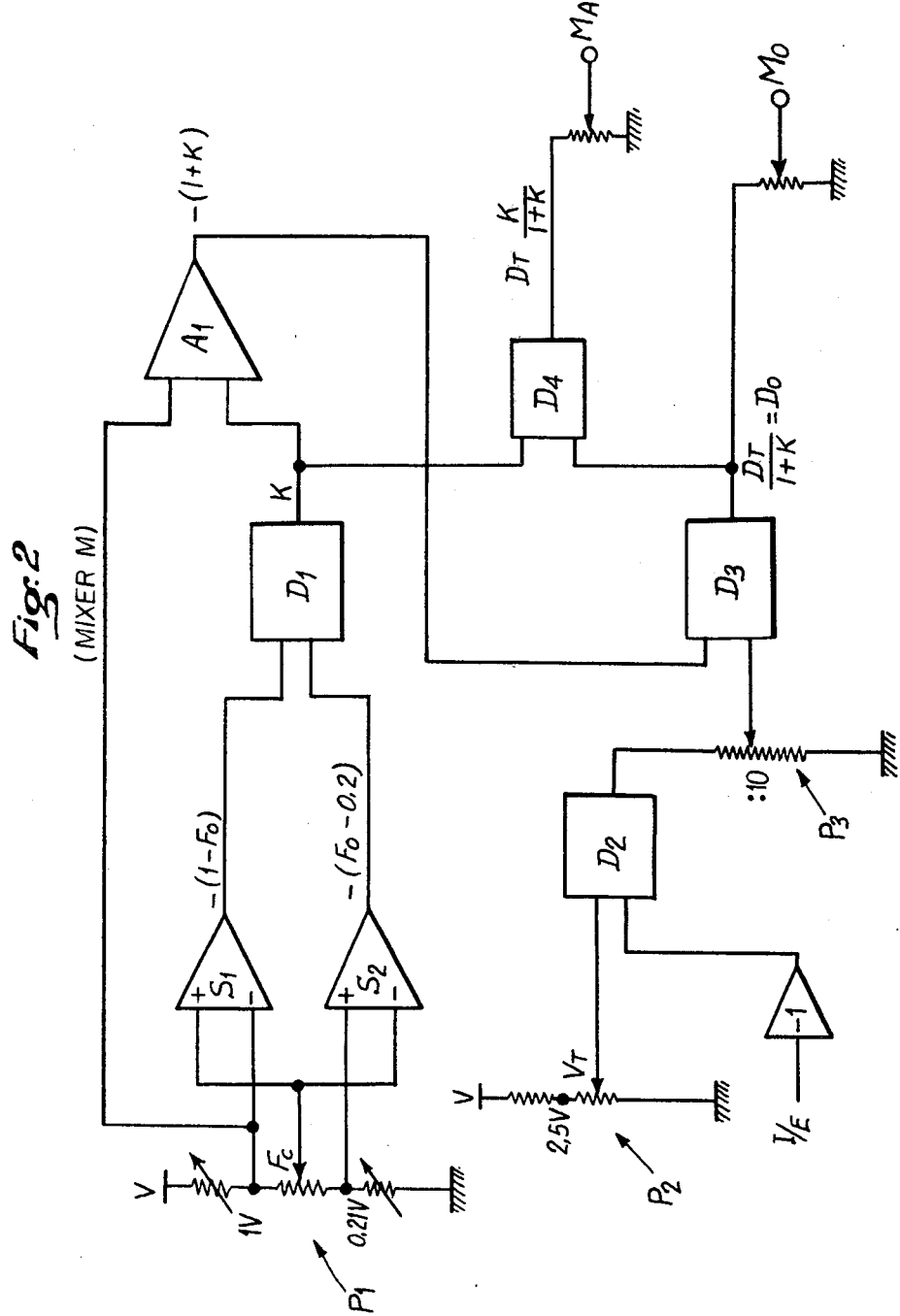
FIG. 2 shows the arrangement of one component of the device in FIG. 1 (Mixer M)

According to one characteristic of the invention, generation of the signals is taken from the application of the formulae. One practical preferred embodiment is shown in FIG. 2. A first potentiometer $P_1$ is used, by the operator, for fixing the percentage of oxygen $F_O$ in the mixture. A stabilised voltage source V is used with two adjusting resistors, and, using potentiometer $P_1$ a voltage $F_O$ is selected which lies somewhere on the range from 0.21 volts to one volt, representing the proportion of oxygen lying between 0.21 for pure air and 1 for pure oxygen. Using two subtracting circuits $S_1$, $S_2$ there are obtained from these three voltages 0.21, $F_O$ and 1 volt, voltages representative of $-(1-F_O)$ and $-(F_O-0.21)$ which are injected into the divider $D_1$ in order to obtain: $(1-F_O)/(F_O-0.21)$ or in other words K. (For reasons of practical convenience, for $S_2$ a subtractor having a relationship of $-10$ can be used, and for $D_1$ a divider having an amplification of 10).

In order to obtain $1+K$, the value K, either directly, or after feeding it into a multiplier receiving a voltage of one volt, is fed to one of the inputs of an adder/inverter $A_1$, the voltage of one volt being fed to the other input. The output from adding circuit $A_1$ then gives a value equal to $-(1+K)$.

A second potentiometer $P_2$ is used for fixing the total gas throughput. Using a resistor and a stabilised voltage source V, the range of adjustment $P_2$ is held between 2.5 volts and O and the operator is thus able to select a voltage $V_T$ representative of the total throughput of the air plus oxygen mixture.

A signal which is directly proportional to I/E provided by the timebase circuit B being supplied by the line BM, is fed into an inverter $(-1)$, and then the signal $V_T$ and the signal $-I/E$ are fed into a divider $D_2$ so that an output signal is produced which is proportional to the amount of flow which should exist during the opening time of the solenoid - control valve, in other words during the inspiration period. By making use of this operation, the fixed total gas throughput is always independent of the ratio I/E selected. The operator thus uses the potentiometer $P_2$ to fix the desired throughput, without concerning himself with the ratio I/E and the divider $D_2$ determines the instantaneous gas throughput as a function of the ratio I/E.

The output signal from divider $D_2$ is fed, via a scale adjusting potentiometer $P_3$, to a divider $D_3$ which moreover receives the signal $-(1+K)$. The output is the signal $D_T/(1+K)$ in other words $D_O$ which is taken off at the contact $M_O$ after setting the potentiometer.

The signal $D_T/(1+K)$ is further fed to an additional divider $D_4$ which receives the signal K at the other input, and this provides as an output the signal $D_T K/(1+K)$ in other words $D_A$ which is taken off at $M_A$ after setting of the potentiometer.

Figure 3:
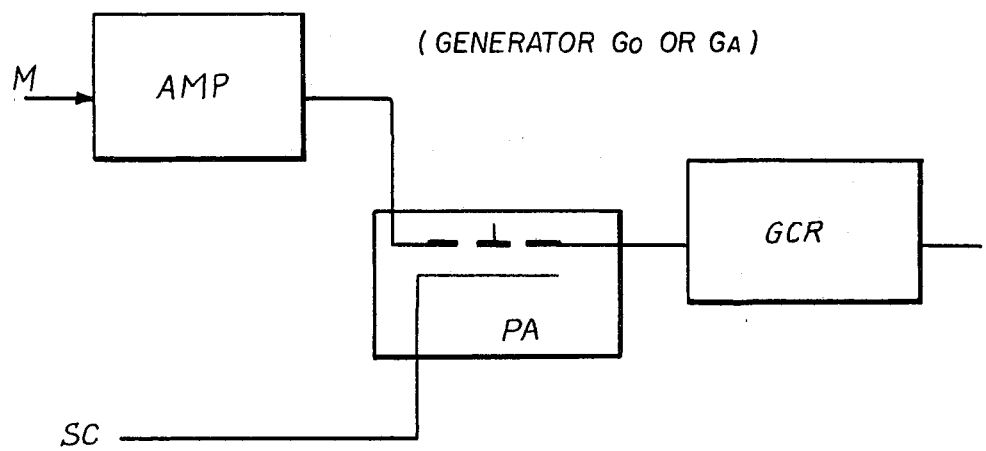
FIG. 3 shows the arrangement of a further component of the device in FIG. 1 (Generator G)

FIG. 3 shows a block diagram of an analogue signal generator producing the product of the signal which is chopped as a function of time supplied by the timebase circuit and of the signal supplied by the gas mixer, so as to furnish signals having three orders of control: frequency, cyclic relationship, amplitude. It will be recalled that the two generators $G_O$ and $G_A$ are identical. A generator includes a rapid switching relay or an analogue gate PA or any equivalent system, controlled by the timebase circuit (line SC). Signal M ($M_O$ or $M_A$) supplied by the mixer is amplified in the amplifier AMP before being fed to the relay. The output from the relay passes through a regulated current generator GCR before being applied to the solenoid-control valve EV.

Figure 4:
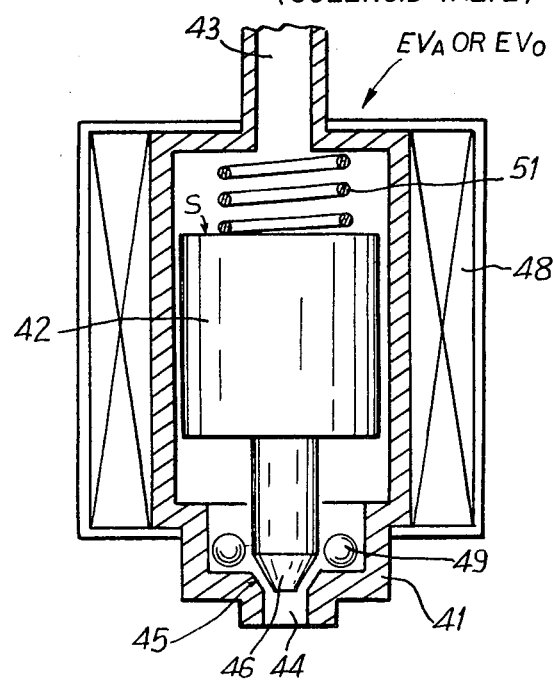
FIG. 4 is a diagrammatical view in section of a further component consisting of one of the valves.

FIG. 4 shows a diagramatical cross-section of one example of a valve which can be used in this device of the present invention. The valve EV has a casing 41 in which a plunger 42 slides. The casing includes a gas entry 43 and an outlet 44 in which a valve seat 45 is provided. A needle 46 cooperates with the seat in order to increasingly open or close the valve as a function of the current flowing in the winding 48. The outside dimension of the plunger and the inside dimension of the casing are accurately defined with respect to each other to leave a peripheral passage for the gas which is admitted at 43 at an accurately fixed pressure. A ball race 49 ensures that the needle 46 is correctly centered. A spring 51 may be provided for returning the valve to a closed position. Generally, the gas pressure on the upper face s of the plunger 42 is sufficient to keep the valve closed when there is no energising current flowing in the winding.

As a function of the gas throughput set and displayed, and the proportion of oxygen in it and as a function of the ratio I/E, the plunger 42 becomes displaced towards the entry 43, through a distance such that an amount of gas flow (air or oxygen) is established through the outlet 44 during the inspiration phase which then allows an amount of gas corresponding to the mean throughput during the period I+E to pass. The aims of the present invention are consequently met in an effective manner.

FIG. 5 shows an example of a complete arrangement of the electronic circuit with indication of the components and their values.

It will of course be understood that the embodiment described above is only an example and that it would be possible to modify this notably by carrying out substitution using equivalent technology without this leading to departure from the scope of the invention.

What I claim is:

1. Control device for an artificial respirator, comprising: a solenoid-controlled valve for air and a solenoid-controlled valve for oxygen, both of said valves being of the variable flow type as a function of the plunger travel, and discharging into a manifold; a timebase circuit for fixing both the respiratory frequency and the ratio I/E of the inhalation time to the exhalation time during each period; a mixer for fixing both the overall respiratory flow and the proportion of oxygen in the gas supplied by the regulator; and two signal generators each linked to and controlling the opening of an associated solenoid-controlled valve; the timebase circuit output being connected to inputs of said generators in order that they may control the opening of the valves during the inhalation time, the generators being further connected to respective outputs of the mixer for receiving signals corresponding to the extent of opening of the valves during the inhalation period, the mixer being connected to the timebase circuit for receiving a signal therefrom corresponding to the ratio I/E to correspondingly adjust signals proportional to respiratory flow and oxygen proportion, whereby the valves are opened to an extent such that during the inhalation period, each valve allows a quantity of gas to pass which corresponds to the mean flow rate during the period.

2. Device according to claim 1 wherein each generator includes a rapid switching relay of the analog gate type, the opening of which is controlled by the timebase circuit.

3. Device according to any one of claims 1 or 2, wherein the mixer includes potentiometers for fixing the respiratory flow and the proportion to oxygen arranged in a manner such as to deliver voltages which are proportional to the desired air and oxygen throughputs, and wherein the assembly is of the analog type, making it possible to obtain values representative of the total gas throughput and on the basis of the latter, of the throughput of air and the throughput of oxygen during the inhalation period.

4. Device according to any one of claims 1 or 2, wherein the mixer includes potentiometers for fixing the respiratory flow and the proportion of oxygen arranged in a manner such as to deliver voltages which are proportional to the desired air and oxygen throughputs, and wherein the assembly is of the logic type, making it possible to obtain values representative of the total gas throughput and on the basis of the latter, of the throughput of air and the throughput of oxygen during the inhalation period.

* * * * *